United States Patent [19]

Takao

[11] Patent Number: 5,298,500
[45] Date of Patent: Mar. 29, 1994

[54] PESTICIDAL O,S-DIALKYL-O-[4-(1-ALKOXY-2,2,2-TRI-FLUOROETHYL)PHENYL]PHOSPHORO(DI) THIOATE DERIVATIVES

[75] Inventor: Hisashi Takao, Tokushima, Japan

[73] Assignee: Otsuka Kagaku Kabushiki Kaisha, Osaka, Japan

[21] Appl. No.: 852,949

[22] Filed: Mar. 17, 1992

[30] Foreign Application Priority Data

Mar. 22, 1991 [JP] Japan .................................. 3-059154

[51] Int. Cl.$^5$ .......................... A61K 31/66; C07F 9/18
[52] U.S. Cl. ..................................... 514/129; 558/194
[58] Field of Search .......................... 558/194; 514/129

[56] References Cited

U.S. PATENT DOCUMENTS 4,576,935 3/1986 Schwarz et al. ..................... 514/113

FOREIGN PATENT DOCUMENTS 2-121996 5/1990 Japan ................................... 558/194

Primary Examiner—Mary C. Lee
Assistant Examiner—M. Ambrose
Attorney, Agent, or Firm—Armstrong, Westerman, Hattori, McLeland & Naughton

[57] ABSTRACT

Disclosed is a phosphoric acid ester derivative represented by the general formula

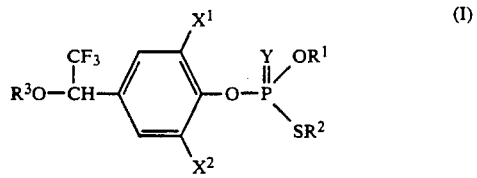

(I)

wherein $R^1$, $R^2$ and $R^3$ are each lower alkyl, $X^1$ and $X^2$ are the same or different and are each a hydrogen atom or halogen atom, and Y is an oxygen atom or sulfur atom. The phosphoric acid ester derivatives of the present invention are usable as insecticides and miticides having excellent residual activity and low toxicity to warm blooded animals.

2 Claims, No Drawings

PESTICIDAL O,S-DIALKYL-O-[4-(1-ALKOXY-2,2,2-TRIFLUORO-ETHYL)PHENYL]PHOSPHORO(DI) THIOATE DERIVATIVES

The present invention relates to novel phosphoric acid ester derivatives, a process for preparing the derivative and insecticidal and miticidal compositions comprising the derivative.

Known organic phosphoric acid ester derivatives include compounds, such as dimethyl 2,2-dichlorovinyl phosphate (brand name: Dichlovos) and 0,0-di-n-propyl 0-4-methylthiophenyl phosphate (brand name: Propahos), which have insecticidal and miticidal activity. Although having high insecticidal and miticidal activity, these compounds have poor residual activity and have high toxicity to warm blooded animals.

Thus, none of the known organic phosphoric acid ester derivatives are usable as insecticides and miticides having excellent residual activity and low toxicity to warm blooded animals.

An object of the present invention is to provide a phosphoric acid ester derivative having excellent insecticidal activity and very high miticidal activity.

Another object of the invention is to provide a phosphoric acid ester derivative having excellent residual activity.

Another object of the invention is to provide a phosphoric acid ester derivative which is extremely low in toxicity to warm blooded animals.

Still another object of the invention is to provide a phosphoric acid ester derivative having high activity also against organic phosphorus resistant insects and mites.

Other features of the invention will become apparent from the following description.

The phosphoric acid ester derivatives of the present invention are novel compounds which have not been disclosed in literature, and are represented by the following general formula (I):

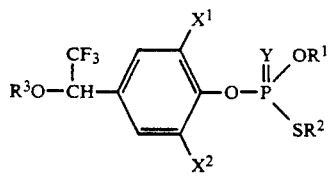

wherein $R^1$, $R^2$ and $R^3$ are each lower alkyl, $X^1$ and $X^2$ are the same or different and are each a hydrogen atom or halogen atom, and Y is an oxygen atom or sulfur atom.

More specifically, the groups or atoms represented by $R^1$, $R^2$, $R^3$, $X^1$ and $X^2$ are as follows.

Examples of useful lower alkyl groups are straight-chained or branched-chain alkyl groups having 1 to 6 carbon atoms, such as methyl, ethyl, n-propyl, isopropyl, n-butyl, isobutyl, sec-butyl, amyl and hexyl.

Examples of halogen atoms are chlorine atom, bromine atom and the like.

The phosphoric acid ester derivatives of the formula (I) can be produced by various processes, typical of which is, for example, the process represented by the following equation-1.

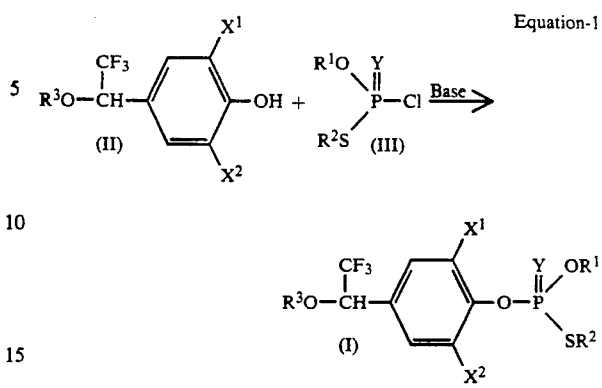

wherein $R^1$, $R^2$, $R^3$, $X^1$ and $X^2$ are as defined above.

Thus, the compounds of the present invention are prepared by reacting a phenol derivative represented by the general formula (II) with a phosphoric acid chloride represented by the general formula (III) in the presence of a base.

This reaction is carried out in an organic solvent or in a two-phase system of an organic solvent and water. Examples of useful organic solvents are ethers such as diethyl ether, dibutyl ether, tetrahydrofuran and dioxane, nitriles such as acetonitrile and propionitrile, ketones such as acetone and methyl ethyl ketone, aromatic hydrocarbons such as benzene and toluene, hydrocarbon halides such as dichloromethane, dichloroethane, chloroform and carbon tetrachloride, etc.

Although the proportions of the phenol derivative of the formula (II) and the phosphoric acid chloride of the formula (III) to be used are not limited specifically but can be suitably determined from a wide range, usually about 0.5 to about 2 moles, preferably about 1 to about 1.5 moles, of the latter is used per mole of the former. Useful bases are a wide variety of those already known. Examples of such bases are triethylamine, pyridine and like tertiary amines, sodium carbonate, potassium carbonate and like alkali metal carbonates, sodium hydroxide, potassium hydroxide and like alkali metal hydroxides, sodium hydride, potassium hydride and like alkali metal hydrides, etc. The base is used in an amount usually of about 1 to about 2 moles, preferably about 1 to about 1.2 moles, per mole of the compound (II). The reaction proceeds favorably usually at 0° to 50° C. and generally takes about 1 to 5 hours for termination.

With reference to Equation-1, the compound (III) for use as one of the starting materials is a known compound which is industrially available at a low cost. The other starting material, i.e., the compound (III), can also be easily prepared, for example, by the known process represented by Equation-2 and Equation-3 given below.

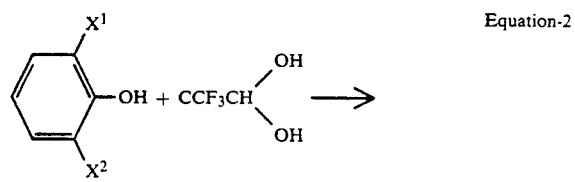

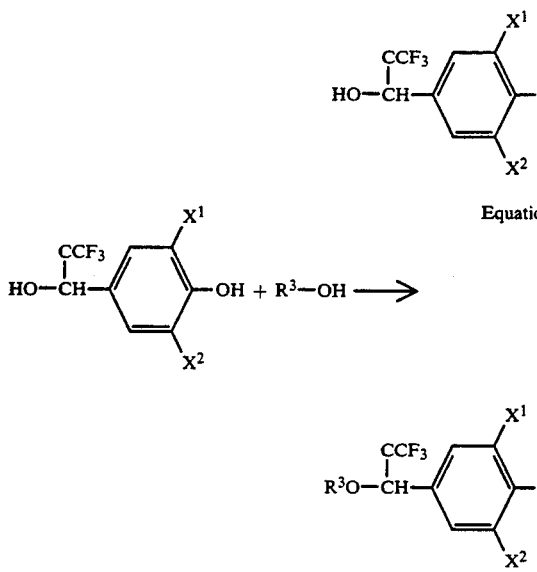

In the above equations, $R^3$, $X^1$ and $X^2$ as defined above.

The reaction of Equation-2 is conducted in the presence of a base, for example, with use of potassium carbonate through the procedure disclosed in detail in Japanese Unexamined Patent Publication SHO 57-146736.

The reaction of Equation-3 is carried out in the presence of a suitable condensing agent such as sulfuric acid by the method disclosed in detail in Org. Syn., Coll. Vol. 4, 72(1963).

The compound of the invention obtained by the foregoing process can be readily isolated from the reaction mixture and purified by a usual separation method, such as solvent extraction, solvent dilution, distillation, recrystallization or column chromatography. The present compound can be prepared in a high yield and with high purity by the production process described.

Typical compounds of the invention obtained in this way are as follows.

0-Ethyl S-n-propyl 0-[4-(α-trifluoromethyl-α-methoxy)-methyl]phenylphosphorothioate (Compound 1)

0-Ethyl S-n-propyl 0-[4-(α-trifluoromethyl-α-methoxy)-methyl]phenyldithiophosphate (Compound 2)

0-Methyl S-iso-butyl 0-[4-(α-trifluoromethyl-α-methoxy)-methyl]phenylphosphorothioate (Compound 3)

0-Ethyl S-n-propyl 0-[4-(α-trifluoromethyl-α-methoxy)-oro]phenylphosphorothioate (Compound 4 )

0-Ethyl S-iso-butyl 0-[4-(α-trifluoromethyl-α-methoxy)-methyl-2-chloro]phenylphosphorothioate (Compound 5)

0-Ethyl S-sec-butyl 0-[4-(α-trifluoromethyl-α-methoxy)-methyl-2-chloro]phenylphosphorothioate (Compound 6)

0-Methyl S-iso-butyl 0-[4-(α-trifluoromethyl-α-methoxy)-methyl-2-chloro]phenylphosphorothioate (Compound 7)

0-ethyl S-n-propyl 0-[4-(α-trifluoromethyl-α-methoxy)-methyl-2,6dichloro]phenylphosphorothioate (Compound 8)

0-Ethyl S-n-propyl 0-[4-(α-trifluoromethyl-α-ethoxy)-methyl-2-chloro]phenylphosphorothioate (Compound 9)

0-Methyl S-iso-butyl 0-[4-(α-trifluoromethyl-α-ethoxy)-methyl-2,6-dichloro]phenylphosphorothioate (Compound 10)

0-Methyl S-iso-butyl 0-[4-(α-trifluoromethyl-α-ethoxy)-methyl-2-chloro]phenylphosphorothioate (Compound 11 )

0-Ethyl S-iso-butyl 0-[4-(α-trifluoromethyl-α-ethoxy)-methyl-2-chloro]phenylphosphorothioate (Compound 12)

0-Ethyl S-n-propyl 0-[4-(α-trifluoromethyl-α-ethoxy)-methyl]phenylphosphorothioate (Compound 13)

0-Ethyl S-n-propyl 0-[4-(α-trifluoromethyl-α-ethoxy)-methyl-2,6-dichloro]phenylphosphorothioate (Compound 14)

0-Methyl S-iso-butyl 0-[4-(α-trifluoromethyl-α-ethoxy)-methyl-2,6-dichloro]phenylphosphorothioate (Compound 15)

0-Ethyl S-n-propyl 0-[4-(trifluoromethyl-α-n-propoxy)-methyl-2-chloro]phenylphosphorothioate (Compound 16)

0-Ethyl S-iso-butyl 0-[4-(α-trifluoromethyl-α-n-propoxy)-methyl-2-chloro]phenylphosphorothioate (Compound 17)

0-Methyl S-iso-butyl 0-[4-(α-trifluoromethyl-α-n-propoxy)- methyl-2-chloro]phenylphosphorothioate (Compound 18)

0-Ethyl S-n-propyl 0-[4-(α-trifluoromethyl-α-n-butoxy)-methyl]phenylphosphorothioate (Compound 19)

0-Ethyl S-n-propyl 0-[4-(α-trifluoromethyl-α-n-butoxy)-methyl-2-chloro]phenylphosphorothioate (Compound 20)

0-Ethyl S-iso-butyl 0-[4-(α-trifluoromethyl-α-n-butoxy)-methyl-2-chloro]phenylphosphorothioate (Compound 21)

0-Methyl S-iso-butyl 0-[4-(α-trifluoromethyl-α-n-butoxy)-methyl-2-chloro]phenylphosphorothioate (Compound 22)

0-Ethyl S-n-propyl 0-[4-(α-trifluoromethyl-α-n-butoxy)-methyl-2,6-dichlorolphenylphosphorothioate (Compound 23)

0-Ethyl S-n-propyl 0-[4-(α-trifluoromethyl-α-ethoxy)-methyl-2-chloro]phenyldithiophosphate (Compound 24)

0-Ethyl S-n-propyl 0-[4-(α-trifluoromethyl-α-n-butoxy)-methyl-2-chloro]phenyldithiophosphate (Compound 25)

0-Ethyl S-n-propyl 0-[4-(α-trifluoromethyl-α-methoxy)-methyl-2-bromolphenylphosphorothioate (Compound 26)

The posphoric acid ester derivatives of the present invention have an excellent insecticidal activity and very high miticidal activity. The present compounds have better residual activity and are more effective on organic phosphorus resistant mites than the conventional organic phosphorus insecticides, and are therefore effectively usable for controlling insects which are harmful to vegetables, fruit trees, etc.

For use as insecticide and miticide, the present compounds can be used in the form of emulsions, hydrated compositions, suspensions, fine particles, powders, wettable powders, coating compositions, foam spray preparations, microcapsules, aerosols, compositions for impregnating natural or synthetic substances, fumigants, concentrates for application in small amounts, etc. In preparing these compositions, various surfactants are usable for emulsifying, dispersing, suspending or foaming purposes. Examples of useful surfactants include nonionic surfactants such as polyoxyethylene alkyl ethers, polyoxyethylene alkyl esters, polyoxyethylene sorbitan alkyl esters and sorbitan alkyl esters, and anionic surfactants such as alkylbenzene sulfonates, alkylsulfosuccinates, alkyl sulfates, polyoxyethylene alkyl sulfates, allylsulfonates and lining sulfite. Usable as dissolving agents, diluents and carriers are various organic solvents, aerosol propellants, natural minerals and vegetables, synthetic compounds, etc. Examples of especially preferable organic solvents are benzene, toluene, xylene, ethylbenzene, chlorobenzene, alkyl naphthalenes, dichloromethane, chloroethylene, cyclohexane, cyclohexanone, acetone, methyl ethyl ketone, methyl isobutyl ketone, alcohols, dimethylformamide, dimethyl sulfoxide, acetonitrile, mineral oil distillates, etc. Examples of useful aerosol propellants are propane, butane, hydrocarbon halides, nitrogen, carbon dioxide, etc. Examples of useful mineral materials are kaolin, talc, bentonite, kieselguhr, clay, montmorillonite, chalk, calcite, pumice, meerschaum, dolomite, etc. Examples of useful vegetables are walnut shells, tabacco stalks, sawdust, etc. Examples of useful synthetic compounds are alumina, silicates, sugar polymers, etc. Examples of tackifying agents are carboxymethylcellulose, gum arabic, polyvinyl alcohol, polyvinyl acetate, etc. Such compositions can be colored with an organic or inorganic dye. The compositions described above are prepared by incorporating the compound of the invention in an amount of about 0.1 to about 95 wt. %, preferably about 0.5 to about 90 wt. %.

The composition prepared is used as it is or as diluted with a carrier or water. In conformity with the contemplated purpose, the composition can be diluted to the range of about 0.00001 to about 100 wt. % as desired. Preferably, the composition is used as so diluted as to contain about 0.0001 to about 10 wt. % of the present compound. Although the amount of the composition to be applied varies with the growth of insects and mites, weather, etc. and can not be determined specifically, it is generally about 0.1 to about 10 kg, preferably about 0.1 to about 1 kg, per hectare calculated as the amount of the present compound.

The present invention will be described in greater detail with reference to the following preparation examples and test examples.

PREPARATION EXAMPLE 1

A 2.0 g quantity (0.01 mole) of 4-(α-trifluoromethyl-α-methoxy)methylphenol and 1.01 g (0.01 mole) of triethylamine were added to 20 ml of methylene chloride. While stirring the mixture with cooling, 2.03 g (0.01 mole) of O-ethyl S-n-propyl phosphoric acid chloride was added dropwise to the mixture. The reaction mixture was thereafter stirred at a temperature of up to 10° C. for 1 hour and washed with 5% aqueous solution of hydrochloric acid, then with saturated aqueous solution of sodium hydrogencarbonate and finally with saturated sodium chloride solution. The mixture was dried over anhydrous magnesium sulfate and distilled to remove the solvent, giving 3.42 g of pale yellow oily O-ethyl S-n-propyl O-[4-α-trifluoromethyl-α-methoxy)-methyl] phenylphosphorothioate (yield 92%).

IR (neat): 1260 cm $^{-1}$ (P=O)

$^1$H-NMR (CDCl$_3$): δppm; 0.8–1.80 (m, 8H, alkyl), 2.56–3.10 (m, 2H, CH$_2$S), 3.40 (s, 3H, CH$_3$O), 3.90–4.50 (m, 2H, CH$_2$O), 4.30–4.80 (q, 1H, CH-CF$_3$), 7.10–7.60 (m, 4H, aromatic H)

The above result indicated that the product was the following compound.

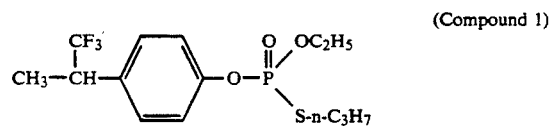

(Compound 1)

PREPARATION EXAMPLE 2

A 2.06 g quantity (0.01 mole) of 4-(α-trifluoromethyl-α-methoxy)methylphenol and 1.38 g (0.01 mole) of anhydrous potassium carbonate were placed into 30 ml of acetonitrile, the mixture was stirred at 40° to 45° C. for 30 minutes and then cooled to room temperature, and 2.18 g (0.01 mole) of O-ethyl S-n-propyl dithiophosphoric acid chloride was added dropwise to the mixture. The reaction mixture was thereafter stirred at 55° to 65° C. for 5 hours, the precipitates were filtered off, and the filtrate was concentrated. The residue was purified on a silica gel column (eluent; benzene:ethyl acetate=10:1), giving 3.41 g of yellow oily O-ethyl S-n-propyl O-[4-(α-trifluoromethyl-α-methoxy)-methyl]-phenyldithiophosphate (yield 88%).

IR (neat): 663, 790 cm$^{-1}$ (P=S)

$^1$H-NMR (CDCl$_3$): δppm; 0.7–1.90 (m, 8H, alkyl), 2.60–3.12 (m, 2H, CH$_2$S), 3.42 (s, 3H, CH$_3$O), 3.90–4.46 (m, 2H, CH$_2$O), 4.30–4.80 (q, 1H, CH-CF$_3$), 7.10–7.60 (M, 4H, aromatic H)

The above result indicated that the product was the following compound.

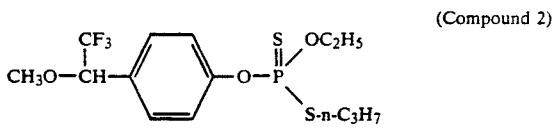

(Compound 2)

The compounds listed in Table 1 were prepared in the same manner as in Preparation Example 1 or 2. Table 1 also shows the properties of the compounds and the spectral data concerned.

TABLE 1

| Compd. No. | Compound | Properties | Spectral data |
|---|---|---|---|
| 3 | CF$_3$ / CH$_3$O—CH—[phenyl]—O—P(=O)(OCH$_3$)(S-iso-C$_4$H$_9$) | Yellow, oil | IR(Neat); 1260 cm$^{-1}$ (P=O) <br> $^1$H-NMR (CDCl$_3$); δ ppm: 0.80–2.20(m, 7H, alkyl), 2.50–3.0(m, 2H, CH$_2$S), 3.40(s, 3H, CH$_3$O), 3.75, 3.95 (s, 3H, CH$_3$O), 4.3–4.8(q, 1H, CH—CF$_3$), 7.10–7.60 (m, 4H, aromatic H) |

TABLE 1-continued

| Compd. No. | Compound | Properties | Spectral data |
|---|---|---|---|
| 4 | CH₃O—CH(CF₃)—[2-Cl-C₆H₃]—O—P(=O)(OC₂H₅)(S-n-C₃H₇) | Pale Yellow, oil | IR(Neat); 1260 cm⁻¹ (P=O)<br>¹H-NMR(CDCl₃); δ ppm: 0.80–2.0(m, 8H, alkyl), 2.60–3.2(m, 2H, CH₂S), 3.40(s, 3H, CH₃O), 3.90–4.50(m, 2H, CH₂O), 4.3–4.8(q, 1H, CH—CF₃), 7.1–7.6(m, 3H, aromatic H) |
| 5 | CH₃O—CH(CF₃)—[2-Cl-C₆H₃]—O—P(=O)(OC₂H₅)(S-iso-C₄H₉) | Pale Yellow, oil | IR(Neat); 1260 cm⁻¹ (P=O)<br>¹H-NMR(CDCl₃); δ ppm: 0.84–2.20(m, 10H, alkyl), 2.60–3.10(m, 2H, CH₂S), 3.40(s, 3H, CH₃O), 3.90–4.50(m, 2H, CH₂O), 4.3–4.8(q, 1H, CH—CF₃), 7.2–7.7(m, 3H, aromatic H) |
| 6 | CH₃O—CH(CF₃)—[2-Cl-C₆H₃]—O—P(=O)(OC₂H₅)(S-sec-C₄H₉) | Pale Yellow, oil | IR(Neat); 1260 cm⁻¹ (P=O)<br>¹H-NMR(CDCl₃); δ ppm: 0.70–2.10(m, 11H, alkyl), 3.08–3.50(m, 1H, CH—S), 3.40(s, 3H, CH₃O), 3.90–4.50(m, 2H, CH₂O), 4.3–4.8(q, 1H, CH—CF₃), 7.20–7.70(m, 3H, aromatic H) |
| 7 | CH₃O—CH(CF₃)—[2-Cl-C₆H₃]—O—P(=O)(OCH₃)(S-iso-C₄H₉) | Pale Yellow, oil | IR(Neat); 1260 cm⁻¹ (P=O)<br>¹H-NMR(CDCl₃); δ ppm: 0.8–2.20(m, 7H, alkyl), 2.50–3.0(m, 2H, CH₂S), 3.40(s, 3H, CH₃O), 3.75, 3.95(s, 3H, CH₃O), 4.3–4.8(q, 1H, CH—CF₃), 7.10–7.70(m, 3H, aromatic H) |
| 8 | CH₃O—CH(CF₃)—[2,6-Cl₂-C₆H₂]—O—P(=O)(OC₂H₅)(S-n-C₃H₇) | Yellow, oil | IR(Neat); 1260 cm⁻¹ (P=O)<br>¹H-NMR(CDCl₃); δ ppm: 0.8–2.20(m, 8H, alkyl), 2.60–3.20(m, 2H, CH₂S), 3.40(s, 3H, CH₃O), 4.0–4.50(m, 2H, CH₂O), 4.3–4.8(q, 1H, CH—CF₃), 7.3(s, 2H, aromatic H) |
| 9 | CH₃O—CH(CF₃)—[2,6-Cl₂-C₆H₂]—O—P(=O)(OCH₃)(S-iso-C₄H₉) | Yellow, oil | IR(Neat); 1260 cm⁻¹ (P=O)<br>¹H-NMR(CDCl₃); δ ppm: 0.80–2.20(m, 7H, alkyl), 2.50–3.0(m, 2H, CH₂S), 3.40(s, 3H, CH₃O), 3.75, 3.95(s, 3H, CH₃O), 4.3–4.8(q, 1H, CH—CF₃), 7.3(s, 2H, aromatic H) |
| 10 | C₂H₅O—CH(CF₃)—[2-Cl-C₆H₃]—O—P(=O)(OC₂H₅)(S-n-C₃H₇) | Pale Yellow, oil | IR(Neat); 1260 cm⁻¹ (P=O)<br>¹H-NMR(CDCl₃); δ ppm: 0.80–2.10(m, 13H, alkyl), 2.60–3.10(m, 2H, CH₂S), 3.36–3.70(m, 2H, CH₂O), 4.0–4.50(m, 2H, CH₂O), 4.3–4.8(q, 1H, CH—CF₃), 7.10–7.60(m, 3H, aromatic H) |
| 11 | C₂H₅O—CH(CF₃)—[2-Cl-C₆H₃]—O—P(=O)(OCH₃)(S-iso-C₄H₉) | Pale Yellow, oil | IR(Neat); 1260 cm⁻¹ (P=O)<br>¹H-NMR(CDCl₃); δ ppm: 0.80–2.20(m, 10H, alkyl), 2.50–3.0(m, 2H, CH₂S), 3.40–3.66(m, 2H, CH₂O), 3.75, 3.95(s, 3H, CH₃O), 4.3–4.8(q, 1H, CH—CF₃), 7.10–7.60(m, 3H, aromatic H) |
| 12 | C₂H₅O—CH(CF₃)—[2-Cl-C₆H₃]—O—P(=O)(OC₂H₅)(S-iso-C₄H₉) | Pale Yellow, oil | IR(Neat); 1260 cm⁻¹ (P=O)<br>¹H-NMR(CDCl₃); δ ppm: 0.8–2.1(m, 13H, alkyl), 2.60–3.10(m, 2H, CH₂S), 3.40–3.62(m, 2H, CH₂O), 4.0–4.50(m, 2H, CH₂O), 4.3–4.8(q, 1H, CH—CF₃), 7.20–7.60(m, 3H, aromatic H) |
| 13 | C₂H₅O—CH(CF₃)—[C₆H₄]—O—P(=O)(OC₂H₅)(S-n-C₃H₇) | Yellow, oil | IR(Neat); 1260 cm⁻¹ (P=O)<br>¹H-NMR(CDCl₃); δ ppm: 0.80–2.0(m, 11H, alkyl), 2.60–3.10(m, 2H, CH₂S), 3.40–3.78(m, 2H, CH₂O), 4.0–4.50(m, 2H, CH₂O), 4.3–4.8(q, 1H, CH—CF₃), 7.1–7.6(m, 4H, aromatic H) |

TABLE 1-continued

| Compd. No. | Compound | Properties | Spectral data |
|---|---|---|---|
| 14 | CF₃, C₂H₅O—CH— attached to benzene ring with Cl (2,6-positions), para-O—P(=O)(OC₂H₅)(S-n-C₃H₇) | Yellow, oil | IR(Neat); 1260 cm⁻¹ (P=O)<br>¹H-NMR(CDCl₃); δ ppm: 0.80-2.0(m, 11H, alkyl), 2.60-3.10(m, 2H, CH₂S), 3.40-3.80(m, 2H, CH₂O), 4.0-4.50(m, 2H, CH₂O), 4.3-4.8(q, 1H, CH—CF₃), 7.30(s, 2H, aromatic H) |
| 15 | CF₃, C₂H₅O—CH— attached to benzene ring with Cl (2,6-positions), para-O—P(=O)(OCH₃)(S-iso-C₄H₉) | Yellow, oil | IR(Neat); 1260 cm⁻¹ (P=O)<br>¹H-NMR(CDCl₃); δ ppm: 0.80-2.20(m, 10H, alkyl), 2.50-3.0(m, 2H, CH₂S), 3.40-3.66(m, 2H, CH₂O), 3.75, 3.95(s, 3H, CH₃O), 4.3-4.8(q, 1H, CH-CF₃), 7.30(s, 2H, aromatic H) |
| 16 | CF₃, n-C₃H₇O—CH— attached to benzene ring with Cl, -O—P(=O)(OC₂H₅)(S-n-C₃H₇) | Pale Yellow, oil | IR(Neat); 1260 cm⁻¹ (P=O)<br>¹H-NMR(CDCl₃); δ ppm: 0.70~2.0(m, 13H, alkyl), 2.60-3.10(m, 2H, CH₂S), 3.36-3.66(m, 2H, CH₂O), 4.0-4.50(m, 2H, CH₂O), 4.3-4.8(q, 1H, CH—CF₃), 7.10-7.60(m, 3H, aromatic H) |
| 17 | CF₃, n-C₃H₇O—CH— attached to benzene ring with Cl, -O—P(=O)(OC₂H₅)(S-iso-C₄H₉) | Pale Yellow, oil | IR(Neat); 1260 cm⁻¹ (P=O)<br>¹H-NMR(CDCl₃); δ ppm: 0.8-2.20(m, 15H, alkyl), 2.60-3.10(m, 2H, CH₂S), 3.30-3.60(m, 2H, CH₂O), 4.0-4.50(m, 2H, CH₂O), 4.3-4.8(q, 1H, CH—CF₃), 7.10-7.60(m, 3H, aromatic H) |
| 18 | CF₃, n-C₃H₇O—CH— attached to benzene ring with Cl, -O—P(=O)(OCH₃)(S-iso-C₄H₉) | Pale Yellow, oil | IR(Neat); 1260 cm⁻¹ (P=O)<br>¹H-NMR(CDCl₃); δ ppm: 0.8-2.20(m, 12H, alkyl), 2.50-3.0(m, 2H, CH₂S), 3.36-3.66(m, 2H, CH₂O), 3.75-3.95(m, 3H, CH₂O), 4.3-4.8(q, 1H, CH—CF₃), 7.10-7.60(m, 3H, aromatic H) |
| 19 | CF₃, n-C₄H₉O—CH— attached to benzene ring, -O—P(=O)(OC₂H₅)(S-n-C₃H₇) | Yellow, oil | IR(Neat); 1260 cm⁻¹ (P=O)<br>¹H-NMR(CDCl₃); δ ppm: 0.70-2.0(m, 15H, alkyl), 2.60-3.10(m, 2H, CH₂S), 3.36-3.66(m, 2H, CH₂O), 3.95-4.50(m, 2H, CH₂O), 4.3-4.8(q, 1H, CH—CF₃), 7.10-7.60(m, 4H, aromatic H) |
| 20 | CF₃, n-C₄H₉O—CH— attached to benzene ring with Cl, -O—P(=O)(OC₂H₅)(S-n-C₃H₇) | Pale Yellow, oil | IR(Neat); 1260 cm⁻¹ (P=O)<br>¹H-NMR(CDCl₃); δ ppm: 0.70-2.0(m, 15H, alkyl), 2.60-3.10(m, 2H, CH₂S), 3.36-3.66(m, 2H, CH₂O), 4.0-4.50(m, 2H, CH₂O), 4.3-4.8(q, 1H, CH—CF₃), 7.10-7.60(m, 3H, aromatic H) |
| 21 | CF₃, n-C₄H₉O—CH— attached to benzene ring with Cl, -O—P(=O)(OC₂H₅)(S-iso-C₄H₉) | Pale Yellow, oil | IR(Neat); 1260 cm⁻¹ (P=O)<br>¹H-NMR(CDCl₃); δ ppm: 0.8-2.20(m, 17H, alkyl), 2.60-3.10(m, 2H, CH₂S), 3.30-3.60(m, 2H, CH₂O), 4.0-4.50(m, 2H, CH₂O), 4.3-4.8(q, 1H, CH—CF₃), 7.10-7.60(m, 3H, aromatic H) |
| 22 | CF₃, n-C₄H₉O—CH— attached to benzene ring with Cl, -O—P(=O)(OCH₃)(S-iso-C₄H₉) | Pale Yellow, oil | IR(Neat); 1260 cm⁻¹ (P=O)<br>¹H-NMR(CDCl₃); δ ppm: 0.80-2.20(m, 14H, alkyl), 2.50-3.0(m, 2H, CH₂S), 3.36-3.66(m, 2H, CH₂O), 3.75, 3.95(s, 3H, CH₃O), 4.3-4.8(q, 1H, CH—CF₃), 7.10-7.60(m, 3H, aromatic H) |
| 23 | CF₃, n-C₄H₉O—CH— attached to benzene ring with Cl (2,6-positions), -O—P(=O)(OC₂H₅)(S-n-C₃H₇) | Yellow, oil | IR(Neat); 1260 cm⁻¹ (P=O)<br>¹H-NMR(CDCl₃); δ ppm: 0.70-2.0(m, 15H, alkyl), 2.60-3.10(m, 2H, CH₂S), 3.36-3.66(m, 2H, CH₂O), 4.0-4.50(m, 2H, CH₂O), 4.3-4.8(q, 1H, CH—CF₃), 7.30(s, 2H, aromatic H) |

TABLE 1-continued

| Compd. No. | Compound | Properties | Spectral data |
|---|---|---|---|
| 24 | CF$_3$ group: C$_2$H$_5$O—CH—(aryl with Cl)—O—P(=S)(OC$_2$H$_5$)(S-n-C$_3$H$_7$) | Yellow, oil | IR(Neat); 663, 790 cm$^{-1}$ (P=S) $^1$H-NMR(CDCl$_3$); δ ppm: 0.7-2.0(m, 11H, alkyl), 2.60-3.10(m, 2H, CH$_2$S), 3.36-3.70(m, 2H, CH$_2$O), 3.90-4.46(m, 2H, CH$_2$O), 4.3-4.8(q, 1H, CH—CF$_3$), 7.10-7.60(m, 3H, aromatic H) |
| 25 | CF$_3$ group: n-C$_4$H$_9$O—CH—(aryl with Cl)—O—P(=S)(OC$_2$H$_5$)(S-n-C$_3$H$_7$) | Yellow, oil | IR(Neat); 663, 790 cm$^{-1}$ (P=S) $^1$H-NMR(CDCl$_3$); δ ppm: 0.70-2.0(m, 15H, alkyl), 2.60-3.10(m, 2H, CH$_2$S), 3.36-3.60(m, 2H, CH$_2$O), 4.0-4.50(m, 2H, CH$_2$O), 4.3-4.8(q, 1H, CH—CF$_3$), 7.10-7.60(m, 3H, aromatic H) |
| 26 | CF$_3$ group: CH$_3$O—CH—(aryl with Br)—O—P(=O)(OC$_2$H$_5$)(S-n-C$_3$H$_7$) | Yellow, oil | IR(Neat); 1260 cm$^{-1}$ (P=O) $^1$H-NMR(CDCl$_3$); δ ppm: 0.80-2.20(m, 7H, alkyl), 2.60-3.2(m, 2H, CH$_2$S), 3.40(s, 3H, CH$_3$O), 3.90-4.50(m, 2H, CH$_2$O), 4.3-4.8(q, 1H, CH—CF$_3$), 7.10-7.60(m, 3H, aromatic H) |

TEST EXAMPLE 1

Test on *Tetranychus urticae*

Two parts by weight of each of the compounds of the invention listed in Table 2 was dissolved in 98 parts by weight of acetone. The solution was diluted to a specified concentration with an aqueous solution containing 0.04% of a spreader (Shin-Linoh, trademark, product of Nihon Noyaku Co. Ltd.) to prepare a liquid preparation. Adults of *Tetranychus urticae* were placed on kidney beans planted in pots, and the preparation obtained above was sprayed onto the plant until the leaves started to drip. Three days later, the mortality was determined. Table 2 shows the result. Each of the compounds in Table 2 is designated by the reference number of the same compound listed in Table 1.

TABLE 2

| Test compound No. | Concentration (ppm) | Mortality (%) |
|---|---|---|
| 4 | 100 | 100 |
| 5 | 100 | 100 |
| 7 | 100 | 100 |
| 11 | 100 | 100 |
| 12 | 100 | 100 |
| 20 | 100 | 100 |
| 22 | 100 | 100 |
| A | 100 | 100 |

A: Acarol (comparative compound)

TEST EXAMPLE 2

Test on *Spodoptera litura*

Two parts by weight of each of the test compounds listed in Table 3 was dissolved in 98 parts by weight of acetone. The solution was diluted to a specified concentration with an aqueous solution containing 0.04% of a spreader (Shin-Linoh, trademark, product of Nihon Noyaku Co. Ltd.). The resulting solution was sprayed onto the leaves of cabbages until the leaves dripped, followed by drying in the air. Third-instar larvae of *Spodoptera litura* were thereafter placed on the leaves and checked for mortality two days layer. Table 3 shows the result.

TABLE 3

| Test compound No. | Concentration (ppm) | Mortality (%) |
|---|---|---|
| 4 | 400 | 100 |
| 7 | 400 | 100 |
| 10 | 400 | 100 |
| 11 | 400 | 100 |
| 16 | 400 | 100 |
| 20 | 400 | 100 |
| B | 400 | 100 |

B: Lannate (comparative compound)

TEST EXAMPLE 3

Test on *Myzus persicae* Sulzer

On the leaves of cabbages planted in vinyl pots within a plastics greenhouse were placed ten adults of *Myzus persicae* Sulzer per pot. A solution of each test compound of Table 4 having a specified concentration was sprayed onto the plant in an amount of 10 ml/3 pots, and the number of insects survived was checked 24 hours later.

Table 4 shows the mortality calculated.

TABLE 4

| Test compound No. | Concentration (ppm) | Mortality (%) |
|---|---|---|
| 5 | 300 | 100 |
| 7 | 300 | 100 |
| 11 | 300 | 100 |
| 12 | 300 | 100 |
| 17 | 300 | 100 |
| 21 | 300 | 100 |
| c | 300 | 100 |

C: Tokuthion (comparative compound)

TEST EXAMPLE 4

Test on *Tetranychus urticae* (OP-resistant strain)

Two parts by weight of each test compound listed in Table 5 was dissolved in 98 parts by weight of acetone. The solution was diluted to a specified concentration with an aqueous solution containing 0.04% of a spreader (Shin-Linoh, trademark, product of Nihon Noyaku Co. Ltd.) to prepare a solution. Adults of *Tetranychyus urticae*, (OP-resistant strain) were placed on kidney beams planted in pots, and the solution prepared as above was sprayed onto the plant until the leaves dripped. Three days layer, the mortality was determined. Table 5 shows the result.

TABLE 5

| Test compound No. | Concentration (ppm) | Mortality (%) |
|---|---|---|
| 5 | 100 | 100 |
| 7 | 100 | 100 |
| 11 | 100 | 100 |
| 12 | 100 | 100 |
| 20 | 100 | 100 |
| 22 | 100 | 100 |
| D | 100 | 30 |

D: Dimethoate (comparative compound)

I claim:
1. A phosphoric acid ester derivative represented by the general formula

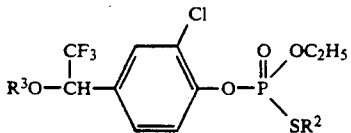

wherein $R_2$ is $C_3$ or $C_4$ alkyl and $R^3$ is methyl or ethyl.

2. An insecticidal and miticidal composition comprising a phosphoric acid ester derivative defined in claim 1 as an active component in combination with an inert diluent or auxiliary.

* * * * *